(12) United States Patent
Yaroslavsky et al.

(10) Patent No.: US 8,139,211 B2
(45) Date of Patent: Mar. 20, 2012

(54) FLUORESCENCE POLARIZATION IMAGING DEVICE AND METHOD

(75) Inventors: Anna N. Yaroslavsky, N. Andover, MA (US); Richard Rox Anderson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/460,596

(22) Filed: Jul. 21, 2009

(65) Prior Publication Data
US 2010/0053607 A1    Mar. 4, 2010

Related U.S. Application Data

(63) Continuation of application No. 11/906,863, filed on Oct. 4, 2007, now Pat. No. 7,564,550, which is a continuation of application No. 10/945,239, filed on Sep. 20, 2004, now Pat. No. 7,289,205.

(60) Provisional application No. 60/504,513, filed on Sep. 19, 2003.

(51) Int. Cl.
   *G01J 3/30* (2006.01)
(52) U.S. Cl. ........................ 356/317; 356/364
(58) Field of Classification Search .................. 356/317, 356/364–370
   See application file for complete search history.

(56) References Cited

U.S. PATENT DOCUMENTS

| | | |
|---|---|---|
| 4,541,438 A | 9/1985 | Parker et al. |
| 4,768,513 A | 9/1988 | Suzuki |
| 5,042,494 A | 8/1991 | Alfano |
| 5,079,262 A | 1/1992 | Kennedy et al. |
| 5,115,137 A | 5/1992 | Andersson-Engels et al. |
| 5,131,398 A | 7/1992 | Alfano et al. |
| 5,205,291 A | 4/1993 | Potter |
| 5,261,410 A | 11/1993 | Alfano et al. |
| 5,270,788 A | 12/1993 | Cercek et al. |
| 5,363,854 A | 11/1994 | Martens et al. |
| 5,413,108 A | 5/1995 | Alfano |
| 5,579,773 A | 12/1996 | Vo-Dinh et al. |
| 5,634,922 A | 6/1997 | Hirano et al. |
| 5,647,368 A | 7/1997 | Zeng et al. |
| 5,929,443 A | 7/1999 | Alfano et al. |
| 6,032,071 A | 2/2000 | Binder |

(Continued)

FOREIGN PATENT DOCUMENTS

GB    2254417 A    10/1992

(Continued)

OTHER PUBLICATIONS

Supplementary European Search Report dated Mar. 9, 2007.

*Primary Examiner* — Tarifur Chowdhury
*Assistant Examiner* — Tara S Pajoohi
(74) *Attorney, Agent, or Firm* — Edwards Wildman Palmer LLP; Peter C. Lauro, Esq.; George N. Chaclas, Esq.

(57) ABSTRACT

The present invention is directed to a novel multi-spectral exogenous fluorescence polarization imaging technique that enables rapid imaging of large tissue fields. The imaging device includes a tunable monochromatic light source and a CCD camera. Linear polarizers are placed into both the incident and collected light pathways in order to obtain fluorescence polarization or/and anisotropy image. To acquire exogenous fluorescence image, fluorescent contrast agents are delivered to a target tissue.

13 Claims, 12 Drawing Sheets
(7 of 12 Drawing Sheet(s) Filed in Color)

U.S. PATENT DOCUMENTS

| | | | |
|---|---|---|---|
| 6,070,093 | A | 5/2000 | Oosta et al. |
| 6,083,487 | A | 7/2000 | Biel |
| 6,091,983 | A | 7/2000 | Alfano et al. |
| 6,091,985 | A | 7/2000 | Alfano et al. |
| 6,123,719 | A | 9/2000 | Masychev |
| 6,135,965 | A | 10/2000 | Tumer et al. |
| 6,175,759 | B1 | 1/2001 | Chan et al. |
| 6,256,530 | B1 | 7/2001 | Wolfe |
| 6,258,576 | B1 | 7/2001 | Richards-Kortum et al. |
| 6,317,624 | B1 | 11/2001 | Kollias et al. |
| 6,352,502 | B1 | 3/2002 | Chaiken et al. |
| 6,587,711 | B1 | 7/2003 | Alfano et al. |
| 6,590,651 | B1 | 7/2003 | Bambot et al. |
| 6,665,556 | B1 | 12/2003 | Alfano et al. |
| 6,674,527 | B2 | 1/2004 | Hoyt |
| 2002/0065468 | A1 | 5/2002 | Utzinger et al. |
| 2003/0026762 | A1 | 2/2003 | Malmros et al. |
| 2003/0158470 | A1 | 8/2003 | Wolters et al. |
| 2003/0163049 | A1* | 8/2003 | Balas ............................ 600/476 |
| 2004/0006275 | A1* | 1/2004 | Demos et al. ................. 600/476 |
| 2004/0006276 | A1 | 1/2004 | Demos et al. |
| 2004/0249274 | A1 | 12/2004 | Yaroslavsky et al. |
| 2006/0132790 | A1 | 6/2006 | Gutin |

FOREIGN PATENT DOCUMENTS

| | | |
|---|---|---|
| JP | 53122489 A | 10/1978 |
| WO | WO-93/13403 A1 A | 7/1993 |
| WO | WO-97/06724 A1 A | 2/1997 |
| WO | WO-01/39665 A2 A | 6/2001 |
| WO | 01/72216 A2 | 10/2001 |
| WO | WO-2006076810 A1 | 7/2006 |

\* cited by examiner

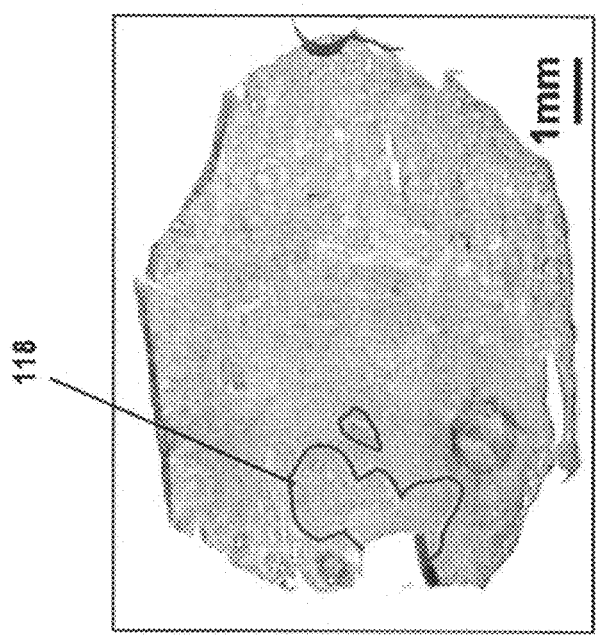
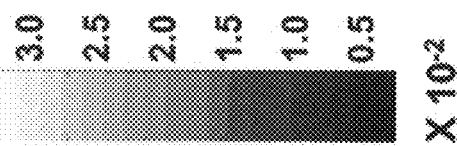
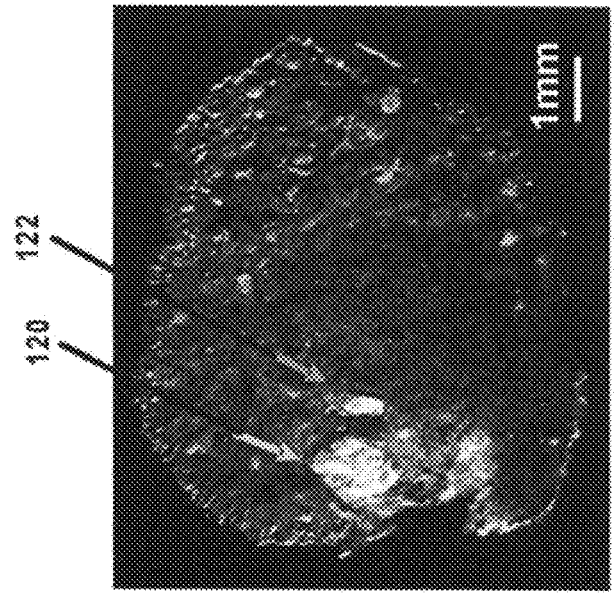
FIG. 9B
FIG. 9A

FLUORESCENCE POLARIZATION IMAGING DEVICE AND METHOD

CROSS-REFERENCE TO RELATED APPLICATION(S)

This application is a continuation of U.S. patent application Ser. No. 11/906,863 filed on Oct. 4, 2007, now U.S. Pat. No. 7,564,550 issued Jul. 21, 2009, which is a continuation of U.S. patent application Ser. No. 10/945,239 filed Sep. 20, 2004, now U.S. Pat. No. 7,289,205 issued Oct. 30, 2007, which claims benefit from U.S. Provisional Application No. 60/504,513, filed Sep. 19, 2003, the disclosures of which are herein incorporated by reference in their entirety.

BACKGROUND OF THE INVENTION

1. Field of the Invention

The present invention is directed to a real-time method for imaging organic tissue. The method employs a polarization-enhanced fluorescence imaging system in order to obtain images of the organic tissue. The obtained images can be used in the demarcation of, among other things, nonmelanoma skin cancers.

2. Background of the Related Art

Nonmelanoma skin cancers are the most common forms of human cancer. About 75% of all skin cancers are basal cell carcinomas (BCC) and about 20% are squamous cell carcinomas (SCC). These cancers are a major cause of morbidity in the Caucasian population. They commonly appear on sun-exposed areas of the body such as the head and neck. Since many tumors occur on the face it is imperative to preserve normal skin surrounding the tumor. Unfortunately, most of these tumors have poorly defined boundaries, which makes visual detection of the tumor borders and, consequently, precise excision a challenging problem.

In the US, Mohs micrographic surgery (MMS) is an accepted procedure that removes as little normal skin as possible while providing the highest cure rate. Using detailed mapping and complete microscopic control of the excised lesion the Mohs surgeon can pinpoint areas at the surgical margins involved with cancer that are otherwise invisible to the naked eye. While precise and accurate, MMS is also a time-consuming and staff-intensive procedure. It requires a surgeon trained in dermatopathology, a dedicated laboratory and a technician to prepare and evaluate frozen sections. Because of these shortcomings, MMS is used in the minority of cases.

In recent years, the development of optical imaging modalities led to the introduction of techniques that may become a viable alternative to the existing methods of skin tumor detection and demarcation. However, all these techniques lack one or more elements necessary for their practical use in a clinical setting.

Confocal reflectance microscopy has been used to study different normal and pathological skin conditions. It allows imaging within turbid media with high resolution (lateral ~1 μm, axial (section thickness) ~3 μm), which is comparable to histology. The major disadvantage of in vivo confocal microscopy for the assessment of skin tumor margins is the small field of view (0.25 mm to 0.3 mm). By sacrificing axial resolution (~30 μm) it is possible to enlarge the field of view up to 2 mm. But even 2 mm field of view is much smaller than the size of most lesions. To examine the entire suspected cancerous area the sequences of images should be captured and stitched together. This process takes time and the resulting image may be distorted by patient's motion.

Polarized light has been used extensively for biological and medical applications. In most cases, skin cancer arises from epidermis. As such, for detection of skin lesions, it is advantageous to acquire superficial images. To achieve this goal while retaining a large field of view polarized light imaging may be employed. The use of polarized light allows imaging of the superficial tissue layers only. When the light incident on the sample is linearly polarized, the two images acquired with the co-polarized and cross-polarized light can be used to largely isolate the single-scattered component, which arises mainly from superficial skin layers. If a turbid medium, like skin, is illuminated with a linearly polarized light, the backscattered light partially retains its polarization. The light that is specularly reflected and single-scattered by a random turbid medium has the same polarization as the incident beam.

For example, let $IM_p^s$ be the intensity of single scattered light at the image plane. Multiple scattering randomizes polarization of the propagating beam. Eventually, half of the multiple backscattered light has the same polarization ($IM_p^m$), and another half has a polarization transversal ($IM_s^m$) to the incident beam polarization, consequently $IM_p^m = IM_s^m$.

Conventional image, IM, is created by single scattered light and multiple scattered light:

$$IM = IM_p^s + IM_p^m + IM_s^m. \qquad (1)$$

An image acquired using the remitted light polarized in the direction parallel to the polarization of the incident light is created by a sum of single scattered light and multiple scattered light:

$$IM_p = IM_p^s + IM_p^m. \qquad (2)$$

An image acquired using the remitted light polarized in the direction transversal to the polarization of the incident light is created by multiple scattered light only:

$$IM_s = IM_s^m. \qquad (3)$$

The difference image, DIM, is obtained by subtraction:

$$DIM = IM_p - IM_s = IM_p^s + IM_p^m - IM_s^m = IM_p^s. \qquad (4)$$

This image is formed by single scattered light since, as it was explained above, $IM_p^m = IM_s^m$.

Single backscattering happens in skin, depending on the wavelength of light, pigmentation, and blood content, at the depth of approximately 70 μm to 200 μm in the visible and near infrared spectral range. Recently, white polarized light digital imaging was being used to evaluate pigmented skin lesions. (Jacques S L, Roman J R, Lee K: Imaging superficial tissues with polarized light. *Las. Surg. Med.* 2000; 26:119-129.) A polarization image, PIM, was created and analyzed:

$$PIM = \frac{IM_p - IM_s}{IM_p + IM_s} \qquad (5)$$

The numerator is equal to DIM. The denominator is a conventional image. The ratio of the difference image to the conventional image can be used to cancel out the contrast that is associated with any superficial chromophore (i.e. melanin, blood) present in the tissue. The thickness of the imaged layer is about 200 μM (white light). Melanin strongly scatters light, producing bright areas with excellent contrast in pigmented lesions. Such high contrast based on scattering would not be expected to occur reliably in nonmelanoma skin cancers, which contain variable amounts of melanin. Thus, this method includes an inability to use spectral information encoded in white light image for lesion characterization and comparatively poor contrast of the nonmelanoma cancer lesion in the image.

Considerable efforts have been devoted to the development of skin tumor imaging techniques based on detection of endogenous fluorescence and exogenous fluorescence of photosensitizers. In Brancaleon et al. the possibility of using autofluorescence (endogenous fluorescence) spectroscopy for the detection of nonmelanoma skin cancer was explored. (Brancaleon L, Durkin A J, Tu J H, Menaker G, Fallon J D, Kollias N: In vivo fluorescence spectroscopy of nonmelanoma skin cancer. *Photochem. Photobiol.* 73(2): 178-183, 2001.) Their in vivo and in vitro studies have shown that the endogenous fluorescence of tryptophan residues was stronger and fluorescence associated with collagen and elastin was weaker in tumor than in normal tissue. At the same time the authors mentioned that in the case of morpheaform BCC, when collagen fibers are surrounded with tumor cells, and SCC in situ, when there is no tumor invasion into the dermis, the collagen fluorescence might increase. The loss of collagen and elastin fluorescence in the vicinity of a tumor was observed for 78% of fresh frozen cancer tissue samples. The areas characterized by the loss of fluorescence were two- to threefold larger than the tumor size determined from histological evaluation. Therefore, the method suggested in the paper may be applied for nonmelanoma cancer detection, but cannot be used for precise tumor demarcation during surgery.

Photodynamic therapy (PDT) has also been tried as an alternative method for treatment of skin cancers. An example of a PDT procedure for dermatology involves the topical application of δ-aminolevulinic acid (ALA) followed by irradiation with red light ($\lambda$~635 nm). ALA is a precursor in the biosynthesis of protoporphyrin IX (Pp IX) that accumulates in tumor tissue. When cells containing Pp IX are irradiated with red light, they are selectively killed. Pp IX is fluorescent, and therefore, may be used for tumor detection.

Wennberg et al imaged in vivo the areas of Pp IX fluorescence and compared the location and the size of these areas with the size of the lesions determined by histological methods. (Wennberg A M, Gudmundson F, Stenquist B, Ternesten A, Moelne L, Rosen A, Larko O: In vivo detection of basal cell carcinoma using imaging spectroscopy. *Acta Derm. Venereol.* 79: 54-61, 1999.) They found that in 50% of lesions the correlation with histology was good, in 23% the correlation was partial, and in 27% there was no correlation at all. The authors noticed that the selectivity of Pp IX fluorescence is not high enough, since in several cases Pp IX fluorescence was detected from sun-damaged skin, healing scars, and normal hair follicles. Similar studies, which employed multi-wavelength fluorescence and lifetime fluorescence imaging, were conducted by several other groups. The predictive capability of Pp IX fluorescence imaging and its ability to demarcate lateral extent of the tumor are still questionable. (Hewett J, Nadeau V, Ferguson J, Moseley H, Ibbotson S, Allen J W, Sibbett W, Padgett M: The application of a compact multi-spectral imaging system with integrated excitation source to in vivo monitoring of fluorescence during topical photodynamic therapy of superficial skin cancers. *Photochem. Photobiol.* 73(3): 278-282, 2001; Andersson-Engels S, Canti G, Cueddu R, Eker C, af Klinteberg C, Pifferi A, Svanberg K, Svanberg S, Taroni P, Valentini G, Wang I: Preliminary evaluation of two fluorescence imaging methods for the detection and the delineation of basal cell carcinomas of the skin. *Las. Surg. Med.* 26:76-82, 2000.)

In many cases the differences of optical signals from normal and diseased tissues are subtle, therefore a lot of effort is devoted to the development and evaluation of novel optical contrast agents. Gold nanoparticles and microspheres filled with light scattering media are examples of such contrast agents. (West J L and Halas N J: Applications of Nanotechnology to Biotechnology—Commentary. *Current Opinion in Biotechnology* 11: 215-220, 2000.) The advantage of these contrast agents is the tunability of their optical properties. In other words, using the structure, the size, and the refractive index as variable parameters it is possible to create the particles, which will enhance scattering and/or absorption of the tissue containing these particles at the specific predefined wavelengths.

The utility of such contrast agents greatly depends on the efficiency of their delivery to the target tumor tissue. One of the approaches is to design very selective contrast agents that could be injected intravenously and that would migrate and localize into a tumor. Another one is to bind the existing contrast agents to specific cell surface proteins thus achieving tumor selectivity. (Bugaj J E, Achilefu S, Dorshow R B, Rajagopalan R. Novel fluorescent contrast agents for optical imaging of in vivo tumors based on a receptor-targeted contrast agent-peptide conjugate platform. *J Biomed Opt* 6:122-33, 2001.)

The development of these state of the art molecular specific contrast agents is a complex and challenging problem. Elaborate and time-consuming animal model testing is required to evaluate the potential of these approaches for in vivo tumor imaging in humans. At this point of development it is not feasible to attempt application of these experimental contrast agents in clinical practice. Where BCC is concerned, investigation of applicability of such molecular-specific agents is even more problematic, since there exists no animal model for BCC of human skin. Therefore an approach based on utilization of the existing contrast agents appears to be more suitable for applications in present clinical settings.

The nontoxic contrast agents that are selectively retained by cancerous tissue have been applied previously to aid in visual examination of oral, bladder, and cervix lesions. Phenothiazinium contrast agents including methylene blue (MB) and toluidine blue (TB) in particular have been used for staining various carcinomas in vivo. (Kaisary A V: Assessment of radiotherapy in invasive bladder carcinoma using in vivo methylene blue staining technique. *Urology*, 28(2): 100-102, 1986; Eisen G M, Montgomery E A, Azumi N, Hatmann D-P, Bhargava P, Lippman M, Benjamin S B: Qualitative mapping of Barrett's metaplasia: a prerequisite for intervention trials. *Gastrointestinal Endoscopy*, 50 (6): 814-818, 1999.) Phenothiazinium contrast agents are accumulated to a much greater extent in mitochondria of carcinoma cells compared to normal cells. (Oseroff A R, Ohuoha D, Ara G, McAuliffe D, Foley J, Cincotta L: Intramitochondrial contrast agents allow selective in vitro photolysis of carcinoma cells. *Proc. Natl. Acad. Sci. USA*, 83: 9729-9733, 1986.) MB has been successfully applied to grossly demarcate neoplastic tumors in bladder, tumors of pancreas, and Barrett's esophagus metaplasia. TB has been used topically to detect oral carcinoma, and Barrett's esophagus metaplasia.

TB is a preferred stain for use in Mohs surgery for BCC, because TB staining provides some advantages relative to hematoxylin-eosin (H&E) including a highly identifiable staining pattern (metachromasia) of BCC. Since TB is routinely used to stain fresh-frozen tissue sections during MMS, the processed polarized light images of stained tumors are remarkably similar to standard Mohs micrographic surgery maps. This similarity significantly simplifies the process of image understanding and interpretation for a Mohs surgeon. Hair follicles, sebaceous glands, fat, and normal stromal elements are visible in detail, and appear differently from the tumor, which appears very dark due to the increased, relative to the normal tissue, uptake of the contrast agent.

Another type of contrast agents used is fluorescent contrast agents (fluorophores). Fluorescent contrast agents absorb light at the specific wavelengths and emit light at longer wavelengths. There are several fluorophores that preferentially stain tumors and, therefore, can be used for tumor detection and demarcation. These include: Pp IX, tetracycline, TB, and MB. Fluorescence spectra are sensitive to the changes in biochemical environment of the fluorophore molecules. Biochemical composition of the diseased skin differs significantly from the normal. Upon excitation with polarized light, the emission from fluorescent samples is also polarized (Lakowic J R: Principles of Fluorescence Spectroscopy: NY, Plenum Press, 1983, Feofilov P P, Irv. Akad Nauk SSSR. Ser. Fiz. 9, 317, 1945, Chen R F and Bowman R L, 1965). This polarization is a result of the photoselection of fluorophores, according to their orientation relative to the direction of the polarized excitation. Fluorescence polarization is defined as $P=(I_{\parallel}-I_{\perp})/(I_{\parallel}+I_{\perp})$.

Alternatively, fluorescence anisotropy, which is defined as $I_r=(I_{\parallel}-I_{\perp})/(I_{\parallel}+2 I_{\perp})$ can be evaluated. To measure fluorescence polarization, the sample is excited with linearly polarized light. When the observing polarizer is oriented parallel ($_{\parallel}$) to the direction of the polarized excitation the observed image (or intensity) is $I_{\parallel}$. When the polarizer is oriented perpendicular ($_{\perp}$) to the polarization plane of the excitation light the observed image is $I_{\perp}$.

Fluorescence emission can be depolarized by a number of phenomena, including rotational diffusion of the fluorophore during the lifetime of the excited state, energy transfer, reabsorption, etc. The dependence of the fluorescence polarization on rotational diffusion led to numerous applications of this technique in biochemical research. For example, fluorescence polarization measurements have been used to study intracellular structural changes, quantify protein denaturation and rotational rates of proteins. There also exist several clinical applications of fluorescence polarization assays. These assays are used for therapeutic drug monitoring, for determination of fetal lung maturity etc. Therefore fluorescence polarization imaging gives a promise of further increasing the specificity of the contrast agents like TB, MB, and TCN.

All of the above mentioned approaches attempted so far for bedside imaging of skin cancer have advantages and drawbacks. It appears, however, that all these techniques lack one or more elements necessary for their practical use in a clinical setting. Thus, confocal microscopy, although providing a superior spatial resolution, suffers from extremely limited field of view and complexity of implementing multi-wavelength imaging.

In addition, this technique is very sensitive to small changes in the position of the investigated object. White-light polarization imaging, being simple and inexpensive, at the same time is unable to use spectral information and as a result does not provide necessary contrast. PpIX-fluorescence imaging is not specific enough; whereas the autofluorescence imaging tends to exaggerate tumor dimensions and is not capable of localizing the morpheaform BCC.

Thus, in view of the above-described deficiencies, a simpler, more accurate and time-efficient method would be desirable for mapping tumor borders.

SUMMARY OF THE INVENTION

The present invention is directed to meeting the aforementioned needs and addressing the deficiencies particularly discussed above and generally in the prior art. The methods, system and apparatus constructed in accordance with the present invention are particularly useful for real-time intraoperative delineation of nonmelanoma skin tumor margins, and provide substantial improvements in standard cancer surgery by, among other things, accelerating the tumor excision process and increasing the number of surgical procedures that can be performed. Furthermore, the present invention can be used to guide the actual tumor excision surgery.

In one embodiment of the present invention, there exists an apparatus for imaging a tissue region. The apparatus includes a polarized light emitter operable to emit light having a wavelength and a first polarization to the tissue region, a light detector operable to detect light remitted from the tissue region having the first polarization and light remitted from the tissue region having a second polarization perpendicular to the first polarization, and an analyzer, used to cut off the excitation wavelength, operable to form a fluorescence image based on said detected light having the first polarization and detected light having the second polarization.

In another embodiment of the present invention, the predetermined wavelength of the polarized light is in a range of 200 nm and 2000 nm (i.e. ultraviolet ("UV")-visible ("VIS")-near infrared ("NIR")).

In yet another embodiment of the invention, the tissue region is stained with a contrast agent. It is envisioned that the contrast agent can be a fluorophore, such as TB, MB tetracycline, PP IX, demeclocycline or the like. The contrast agent can be applied in any suitable manner, such as by topical application prior to surgery as well as by injection into the tumor site.

In yet another embodiment of the invention, there exists an imaging method for imaging a tissue region. The method includes the steps of dying said tissue region with a fluorescent contrast agent, emitting light having a wavelength, corresponding to the absorption band of the dye and a first polarization direction to the tissue region, detecting fluorescence light remitted from the tissue region having said first polarization direction and light remitted from the tissue region having a second polarization direction perpendicular to said first polarization direction, and forming a fluorescence polarization image based on said detected light having said first polarization direction and said detected light having said second polarization direction.

In yet another embodiment of the invention, there exists an imaging method for imaging a tissue region. The method includes the steps of emitting light having a wavelength, corresponding to the absorption band of the dye and a first polarization direction to the tissue region, detecting endogenous fluorescence light remitted from the tissue region having said first polarization direction and light remitted from the tissue region having a second polarization direction perpendicular to said first polarization direction, forming a background fluorescence polarization image based on said detected light having said first polarization direction and said detected light having said second polarization direction, dying said tissue region with a fluorescence contrast agent, detecting fluorescence light remitted from the dyed tissue region having said first polarization direction and light remitted from the dyed tissue region having a second polarization direction perpendicular to said first polarization direction, forming a fluorescence polarization image based on said detected light having said first polarization direction and said detected light having said second polarization direction, and forming a net fluorescence polarization image (i.e., exogenous fluorescence polarization image) based on said background fluorescence polarization image (i.e. endogenous fluorescence polarization image) and said total fluorescence polarization image.

Further features of the subject invention will become more apparent from the detailed description that follows taken in conjunction with the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that those having ordinary skill in the art to which the present application appertains will more readily understand how to make and use the same, reference may be had to the drawings wherein:

FIG. 9a-9b depicts images, including images obtained by the system of FIG. 7, (a) fluorescence polarization and fluorescence polarization scale and (b) histological frozen section, respectively, of BCC stained with 0.05 mg/ml aqueous solution of TB, wherein the tumor is outlined by a Mohs surgeon in FIG. 9(b);

DETAILED DESCRIPTION OF THE INVENTION

In the following detailed description of the present invention, references are made to the accompanying drawings which form a part hereof, and in which is shown by way of schematic illustrations exemplary embodiments of the present invention. These schematic illustrations are not necessarily intended to portray the exact configuration of a system or apparatus constructed in accordance with the present invention. However, one skilled in the art will readily appreciate that the figures along with the description herein are in sufficient detail to enable those skilled in the art to practice the invention.

Figure 1:
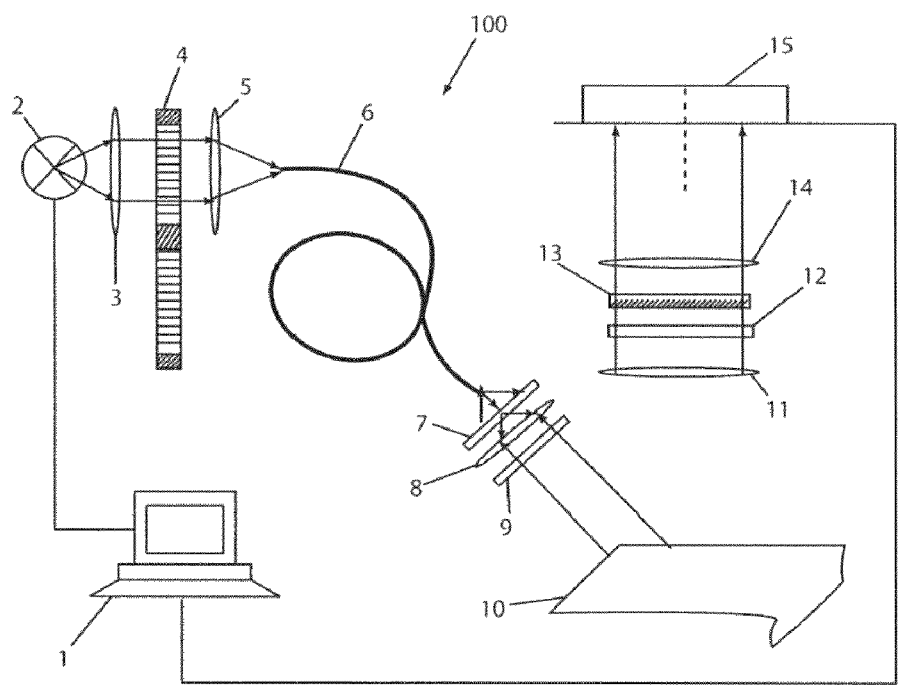
FIG. 1 is a schematic of an exemplary embodiment of an imaging apparatus constructed in accordance with the present invention.

As shown in FIG. 1, a computer 1 controls the imaging apparatus 100 to obtain images of organic tissue 10 such as non-melanoma skin cancers. Specifically, the computer 1 controls a lamp 2, such as a Xenon arc lamp, to emit light. The light passes through a lens 3 to a filter wheel 4. The filter wheel 4 may be provided with a number of interference filters to enable automatic wavelength selection and scanning. In a preferred embodiment, the interference filters will cover the spectral range from 390 nm to 750 nm. The monochromatic light produced by the filter wheel is coupled into a light guide 6, such as a liquid light guide, by a converging lens 5.

At the end of the light guide 6, the monochromatic light passes through a diffusor 7, such as a holographic diffusor, a collimator 8, such as a collimating achromatic lens, and a polarizer 9, such as a linearly polarizing filter. By passing the monochromatic light through the diffusor 7, collimator 8, and polarizer 9, homogeneous polarized light illumination of the tissue 10 can be achieved. The polarized light remitted from the tissue 10 passes through a lens 11, a filter 12, a polarizer 13, and a lens 14 is focused incident on to a charge coupled device (CCD) camera 15. The filter 12 and/or polarizer 13 may be appropriately selected to allow for the study fluorescence emission and/or polarization of the tissue images.

As discussed, although endogenous fluorescence polarization spectroscopy is suitable for cancer detection, the differences of the optical signals from healthy and cancerous tissues are often subtle, and thus, it is necessary to improve the contrast of the diseased areas in the image.

In an embodiment of the present invention, tissue 10 is stained with a fluorescent dye such as toluidine blue O (TBO) and tetracycline (TCN) before images of the tissue 10 are obtained by the imaging apparatus 100. Fluorescence polarized light imaging (FPLI) is well suited for cancer detection. The advantages of this technique include real-time imaging, flexibility, and comparatively low cost. In many cases, however, the differences of optical signals from normal and diseased tissues are subtle, therefore for the reliable assessment of the abnormalities, it is important to improve the contrast of the diseased areas in the images.

Before the tissue 10 is stained with a fluorescent dye, a background or endogenous fluorescence image is obtained using light emitted from the tissue 10. The emitted light is polarized in a plane parallel ($I^b_\parallel$) and perpendicular ($I^b_\perp$) to the polarization plane of the incident light and is focused into CCD 15. Computer 1 receives $I^b_\parallel$ and perpendicular $I^b_\perp$ from CCD 15 and calculates a background fluorescence anisotropy image $I^b_r=(I^b_\parallel-I^b_\perp)/(I^b_\parallel+2I^b_\perp)$, and background fluorescence image $I^b=I^b_\parallel+I^b_\perp$.

After the background fluorescence image and background fluorescence anisotropy image is obtained, a tumor specific fluorescent dye is applied or injected onto/into the tissue 10. The excess dye is rinsed off and fluorescence images are acquired using the light emitted by a fluorophore polarized in a plane parallel ($I_\parallel$) and perpendicular ($I_\perp$) to the polarization plane of the incident light. Once again, the CCD 15 receives the light emitted by the fluorophore and polarized in the plane parallel ($I_\parallel$) and perpendicular ($I_\perp$) to the polarization plane of the incident light and transmits the data to computer 1. Computer 1 creates a fluorescence anisotropy image $I_r=(I_\parallel-I_\perp)/(I_\parallel+2I_\perp)$ and a fluorescence image $I=I_\parallel+I_\perp$.

Computer 1 calculates the net fluorescence image ($I^{net}$) by subtracting the background fluorescence image from the fluorescence image ($I-I^b$) and calculates the net fluorescence anisotropy image ($I^{net}_r$) according to the equation $(I_r I-I^b_r I^b)/$ $I^{net}$. The net fluorescence anisotropy image may be converted to a net fluorescence polarization image ($I^{net}_p$) according to the equation 3 $I^{net}_r/(2+I^{net}_r)$. The resulting image may also be normalized to use the dynamic range of the imaging apparatus 100.

The above-described procedure is used to improve the contrast in tissue 10, when the tissue emits a significant amount of background fluorescence. However, if background fluorescence is negligible the procedure may be simplified because the background fluorescence image and background fluorescence anisotropy image are not obtained prior to the application or injection of a tumor specific fluorescent dye onto/into the tissue.

In this case fluorescence images are acquired as previously described. The light emitted by a fluorophore is polarized in a plane parallel ($I_\|$) and perpendicular ($I_\perp$) to the polarization plane of the incident light and received by CCD 15. A difference image $I_\delta = I_\| - I_\perp$, polarization image $I_{pol} = I_\| - I_\perp/I_\| + I_\perp$, or anisotropy image $I_r = I_\| - I_\perp/I_\| + 2 I_\perp$ created by computer 1 using data transmitted thereto by CCD 15. The resulting images may be normalized to optimally use the dynamic range of the imaging device.

The imaging apparatus employs a computer program to perform PLI or FPLI. The computer program may be stored on a recording medium such as, but not limited to, a tape medium, a disk recording medium, a flash memory, etc.

EXAMPLES

The present invention will be further described by referring to FIGS. 5-9, which depict images of tissues acquired by the PLI method. As will be readily apparent, applying contrast agents, such as MB and TB, greatly improves the contrast of the tumor within the image.

Image of tissue acquired by the FPLI method will be further described by referring to FIGS. 2-6. As will be readily apparent, applying fluorescent contrast agents, such as TBO and TCN, greatly improves the contrast of the tumor within the image.

Figure 2:
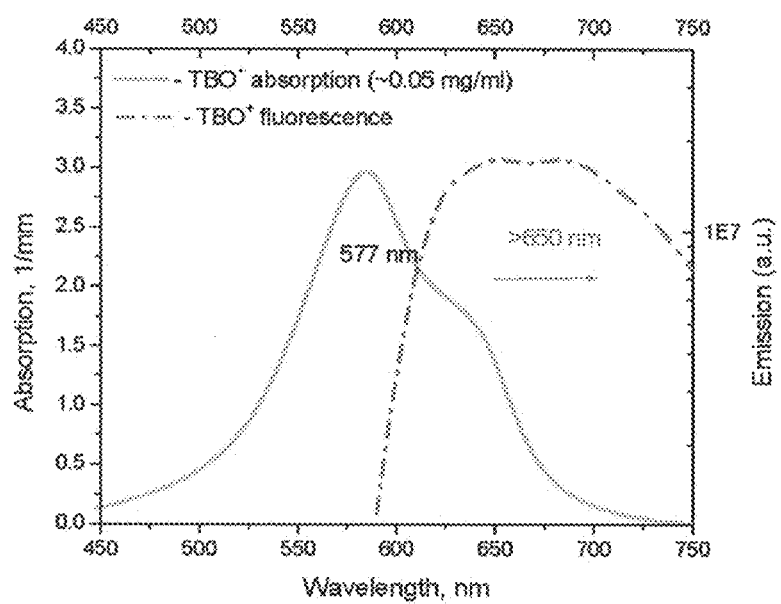
FIG. 2 depicts the excitation (absorption) and emission spectra of TBO (excited at 577 nm)
Figure 3:
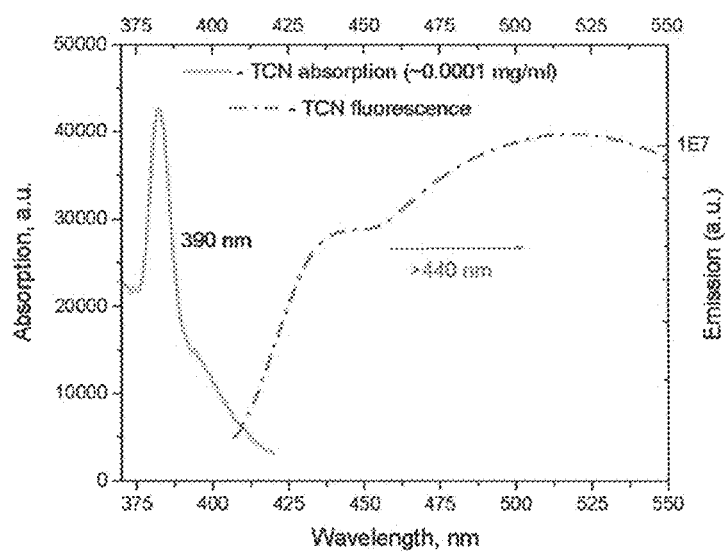
FIG. 3 depicts the excitation (absorption) and emission spectra of TCN (excited at 390 nm)
Figure 4A:
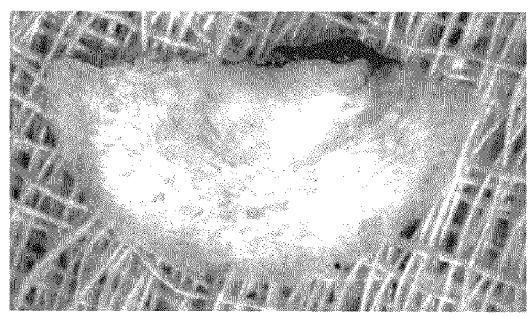
FIG. 4a-4d depicts moderately-differentiated SCC (FOV: 25 mm×6 mm), including obtained images by the system of FIG. 1.
Figure 4B:
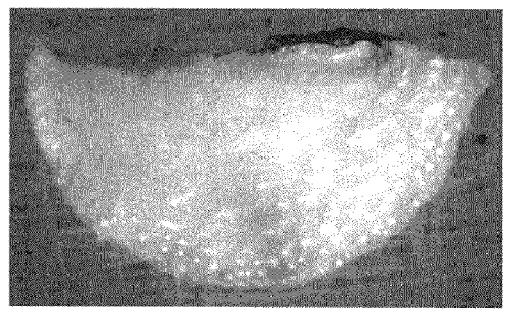
Figure 4C:
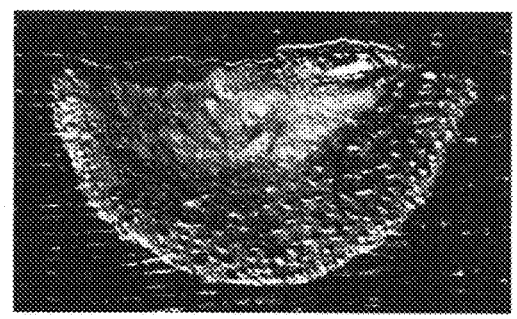
Figure 4D:
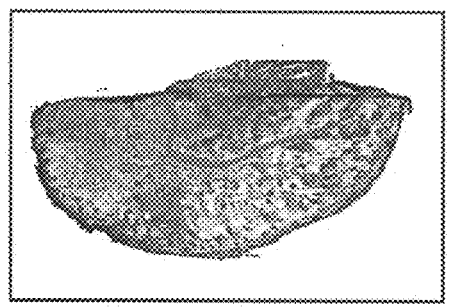

TCN is a highly fluorescent antibiotic. The fluorescence of TBO can be readily detected also. The absorption and fluorescence emission spectra of TBO and TCN are shown in FIGS. 2 and 3, respectively. Commercially available TBO (TB 1% AQ, LC26165-1, Fischer Scientific Company, USA) and tetracycline were used to stain the tissue.

An additional filter was introduced in front of the CCD 15 of imaging apparatus 100 to cut-off the excitation light. Excitation wavelength for TBO was 577 run, and the fluorescence images were acquired at the wavelengths longer than 650 nm. Excitation wavelength of 390 nm was used for tetracycline. Fluorescence images were acquired for the wavelengths longer than 440 nm (maximum: 2.8 cm×2.5 cm), and lateral resolution of approximately 15 µm. Two images were acquired using the remitted light polarized in the directions parallel ($I_\|$) and perpendicular ($I_\perp$) to the polarization of incident light. Then the difference image, FPLI, ($I_\delta = I_\| - I_\perp$) was processed and used as a measure of fluorescence depolarization in tissue.

Processed images were compared to horizontal histological sections. The sections were prepared by Mohs histotechnician during the surgery in the following way. Tissue removed from patients undergoing non-melanoma skin cancer treatment was frozen in optimal cutting temperature compound and processed in the standard horizontal sectioning technique of Mohs [Mohs, 1941, Mikhail, 1991]. Five micron thick sections were transferred to glass slides and stained with hematoxylin-eosin (H&E). These frozen sections were then analyzed for residual tumor at the margins. The last frozen section generated during the procedure was then compared to the superficial images of the remaining discarded piece of excision obtained using the technique described above. Examples FPLI images are compared with histology in FIGS. 4-6.

In FIG. 4 the images of moderately-differentiated SCC tumor are presented. In FIG. 4a conventional reflectance image of the tumor acquired at 620 nm is shown. The tumor can be hardly delineated in this image. In fluorescence image (FIG. 4b) of the tissue stained using TBO the concentration of the dye is very high everywhere, therefore the whole specimen is very bright, and the tumor is not visible. FIG. 4c presents FPLI of the same tumor sample. It is apparent from the image that the remitted fluorescence is much more depolarized by the healthy tissue then by the cancerous. Comparison to histopathology (FIG. 4d) shows good correlation of the bright area in the FPLI and the tumor outlined using red marker by the Mohs surgeon.

Figure 5A:
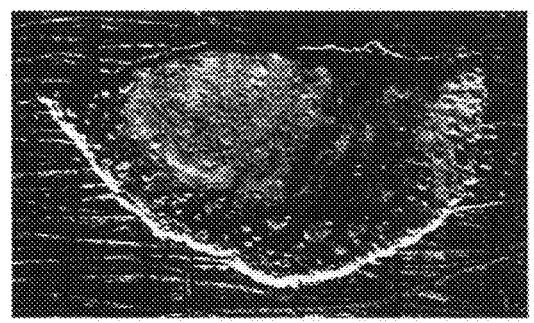
FIG. 5a-5b depicts well-differentiated SCC (FOV: 25 mm×10 mm), including images obtained by the system of FIG. 1.
Figure 5B:
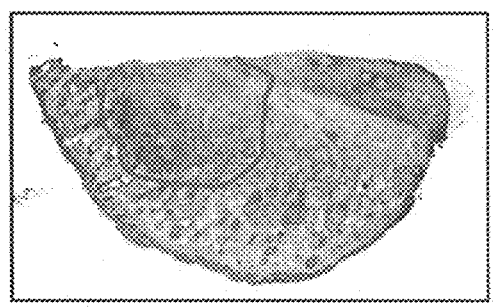

A comparison of the TCN FPLI of the thick cancerous (SCC) skin excision and histopathology is presented in FIGS. 5a and 5b, respectively. FIG. 5a depicts an image obtained by FPLI where the tissue was stained with TCN. FIG. 5b is a histological H&E frozen section prepared during Mohs surgery (section thickness-6 µm). Tumor margins determined by Mohs surgeon are shown with a red line. As in the previous figures, the contrast of the tumor in the image is high and the tumorous area outlined in FPLI correlates well with the one marked by the surgeon in the frozen section.

Figure 6A:
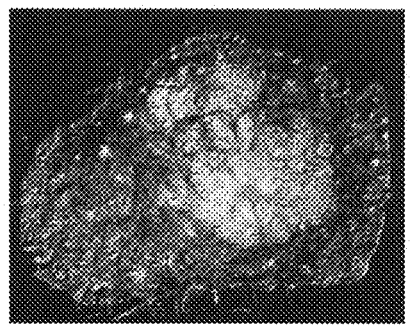
FIG. 6a-6b depicts nodular BSS (FOV: 27 mm×20 mm), including images obtained by the system of FIG. 1.
Figure 6B:
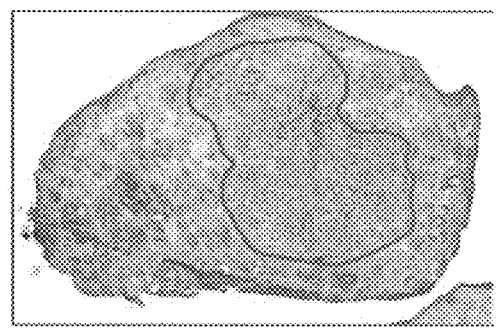

Another example of the FPLI of the nodular BCC stained with TBO is shown in FIG. 6a. FIG. 6b shows the histological H&E frozen section prepared during Mohs surgery (section thickness~5 µm). When compared with the frozen section (FIG. 6b) one can readily see that FPLI obtained images reliably demarcate the tumor.

In total, 20 samples of BCC (including nodular, micronodular, and infiltrative), and SCC (including moderately— and well—differentiated) were imaged so far. Out of 20, 15 samples were stained using TBO and 5 using TCN. In all the cases the tumors could be easily identified in the image and fluorescence polarization images (FPLIs) correlated well with histopathology. FPLI were diagnosed independently of the histologic images. The intensity of endogenous fluorescence of all the samples was much lower than the intensity of the exogenous fluorescence of the dyes (i.e. TBO and TCN) and comparable to noise level. Therefore, autofluorescence presented no problems.

The images presented in FIGS. 4-6 demonstrate how exogenous fluorescence polarization imaging enables differentiation of the cancerous tissue areas. An effective discrimination could be achieved because the fluorescence is depolarized differently by normal and diseased tissue due to differences in biochemical composition.

The results indicate that exogenous fluorescence polarization imaging can accurately delineate the margins of different types of nonmelanoma cancers, including the morphea-form BCC. The rapid acquisition of these images during surgery can potentially allow tumor removal to progress without taking time to process frozen sections, the most time consuming step in MMS. A layer of tumor can be removed, the surgical bed can be imaged, residual tumor can be detected, and guided tumor removal can take place.

Figure 7:
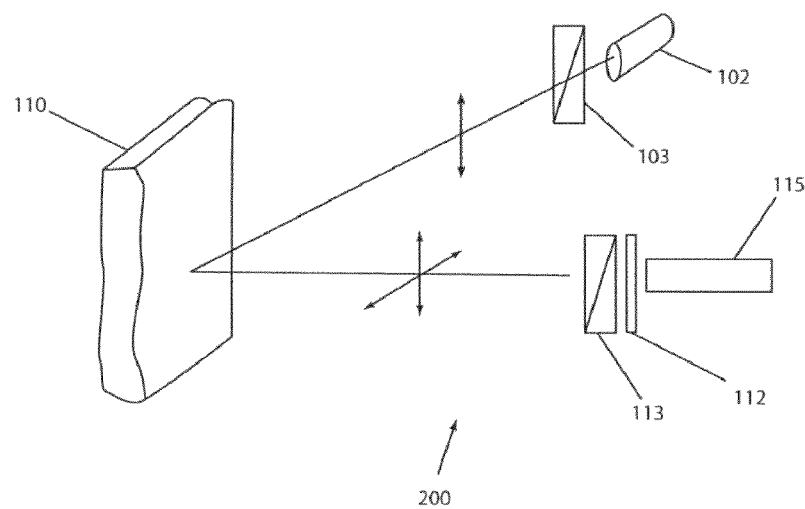
FIG. 7 is a schematic diagram of another exemplary embodiment of an imaging apparatus constructed in accordance with the present invention.

FIG. 7 illustrates another embodiment of an imaging system 200 constructed in accordance with the present invention, in which lamp 102 is a monochromatic light source, preferably a Xenon lamp combined with one or more interference filters as the excitation source which directs light toward tissue sample 110. Linearly polarizing filter lens 103 is in the pathway of incident light directed at tissue 110. Light remitted from tissue 110 passes through polarizer lens 113 and filter 112 before being collected by the imaging device, namely CCD camera/analyzer 115.

CCD 115 is rotated to allow imaging of light polarized in planes parallel ($I_\parallel$) and perpendicular ($I_\perp$) to the polarization plane of incident light. Filter 112 is placed in front of CCD 115 to reject elastically scattered light. This embodiment of the present invention provided a large field of view of about 2.8 cm×2.5 cm and rapid image acquisition. Integration time on the CCD array did not exceed 10 seconds. The lateral resolution of the system was measured to be about 15 μm. The axial resolution (the optical thickness of the section) depends on the optical properties of skin at given wavelength. In the present example, i.e. for human dermis in the wavelength range from 650 nm to 750 nm, it is about 200 μm$^3$.

Methods of the present invention were tested using 15 thick, freshly excised BCC and SCC specimens obtained from Mohs surgery under an Institutional Review Board approved protocol. The lateral size and thickness of investigated samples varied from about 5 to 30 mm, and from about 5 to 20 mm, respectively. The sizes of the tumors were in the range from about 0.35 mm to 15 mm. In this example, TB and MB were used to stain skin excisions. Tumor samples were imaged before dye application to assess the level of skin autofluorescence.

For imaging, tissue samples were placed in a Petri dish on moist gauze and covered with a cover slip. Endogenous fluorescence at the wavelengths longer than 650 nm was found to be negligible. Skin excisions were submerged for up to 15 minutes into 0.05-0.25 mg/ml aqueous solutions of TB or MB, which are commercially available, e.g., MB, 1% injection, USP, American Regent Laboratories, inc., USA and TB, 1% AQ, LC26165-1, Fischer Scientific Company, USA.

After staining, the sample tissue was rinsed and imaged again. Fluorescence of TB and MB was excited at 577 nm and 620 nm, respectively. The incident power density did not exceed 0.15 mW/cm$^2$. The images were acquired in the wavelength range from 650 nm to 750 nm. All experiments were performed at room temperature.

As discussed above, the fluorescence polarization image (FPI) is defined as $P=(I_\parallel-I_\perp)/(I_\parallel+I_\perp)$. To evaluate the accuracy of the suggested method each resulting FPI was compared to the last histological frozen section processed during Mohs surgery. Ideally, this frozen section should be the mirror image of the FPI acquired from the remaining piece of tissue. However, the thickness of the fluorescence optical section is ~200 μm, which is 40 times thicker than the histological section. Therefore, quantitative comparison of the two is not straightforward. Yet, qualitative comparison of the FPI and histology did not represent a problem because morphological features were very similar and easily recognizable.

To provide quantitative assessment of accuracy, the surface areas occupied by the tumor in the FPI ($S_{fpi}$) and histological slides ($S_h$) were compared. The agreement was considered acceptable if the imaged tumor area was equal or up to 10% greater than that of histology ($1 \leq S_{fpi}/S_h < 1.1$), i.e., would correspond to complete tumor removal by image-guided surgery.

Figure 8A:
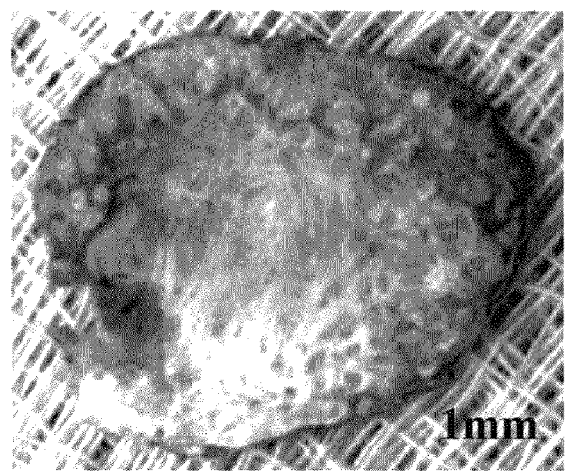
FIG. 8a-8b depicts images, (a) reflectance and (b) fluorescence intensity, respectively, of a BCC tissues sample stained with 0.05 mg/ml aqueous solution of TB, including images obtained by the system of FIG. 7.
Figure 8B:
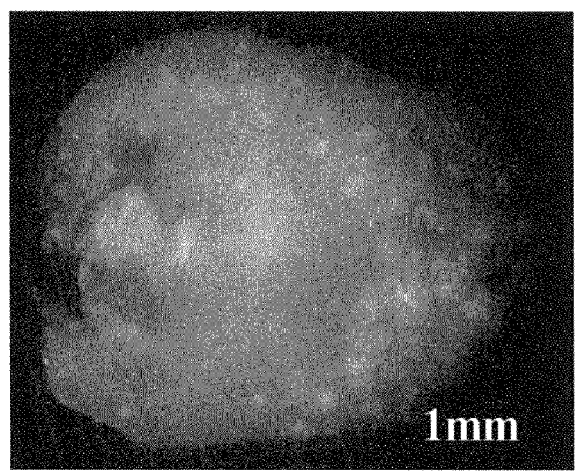

The images of two representative cancer excisions before and after staining are presented in FIGS. 8, 9, and 10. In FIG. 8 reflectance and fluorescence intensity images of nodular BCC tumor are shown. Reflectance image acquired at 577 nm before staining with TB (0.05 mg/ml) (FIG. 8a) demonstrates that the contrast of tumor compared to normal tissue is insufficient for reliable discrimination. Due to the high concentration of TB, fluorescence is observed even in healthy tissue and the tumor can not be demarcated in the fluorescence intensity image (FIG. 8b).

In FIGS. 9a and 9b, the pseudo-color FPI of the same tumor is compared to corresponding histopathology. The tumor is bright compared to the adjacent healthy skin, which means that the remitted fluorescence is much more depolarized in healthy tissue than in cancerous. The values of fluorescence polarization averaged over the cancer and normal tissue areas are $(2.7\pm0.3)\times10^{-2}$ and $(1.0\pm0.7)\times10^2$, respectively. Comparison to histopathology shows good correlation of the bright areas in the FPI and the tumor, outlined using red marker by the Mohs surgeon and indicated by arrow 118. For the larger tumor shown with arrow 120 (FIG. 9a) the ratio of $S_{fpi}/S_h$ is 1.04, and for the smaller tumor lobule shown with arrow 122 $S_{fpi}/S_h$=1.07.

Figure 10B:
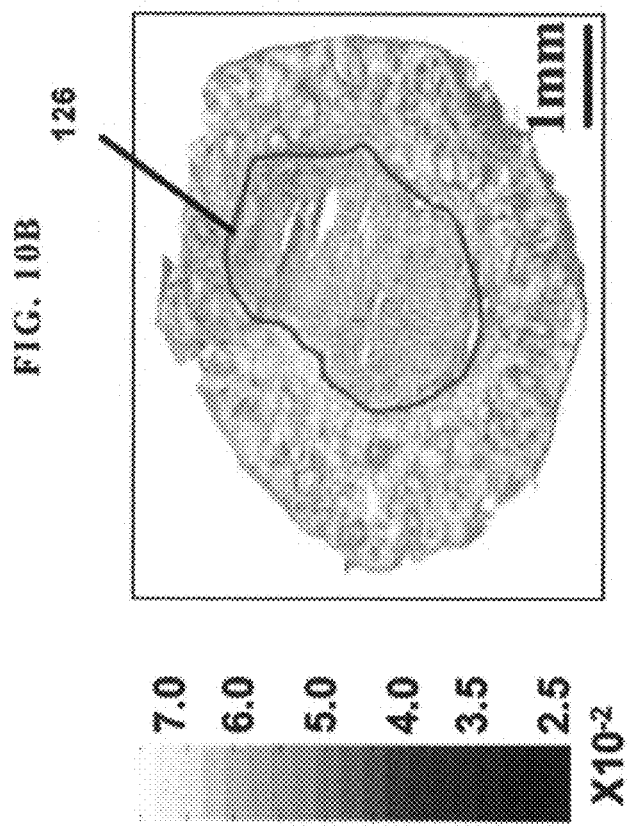
FIG. 10a-10b depicts images, including images obtained by the system of FIG. 7, (a) fluorescence polarization and fluorescence polarization scale and (b) histological frozen section, respectively, of BCC stained with 0.25 mg/ml aqueous solution of MB, wherein the tumor is outlined by a Mohs surgeon in FIG. 10(b)
Figure 10A:
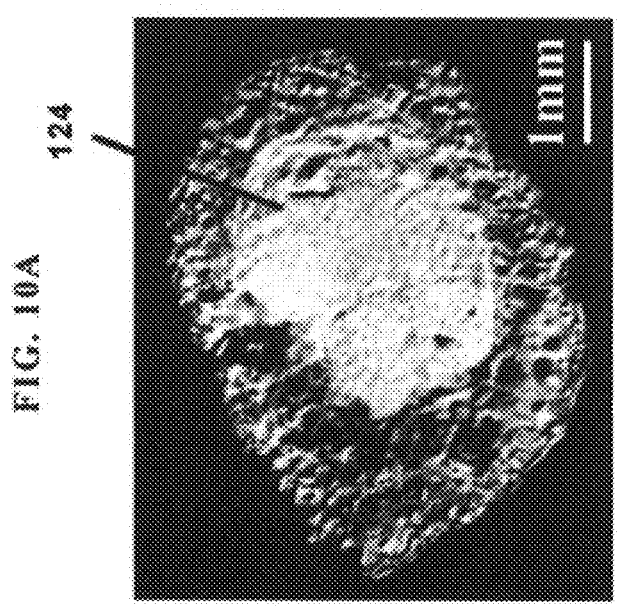

FIGS. 10a and 10b illustrate a comparison of the pseudo-color FPI of BCC excision stained using MB (0.25 mg/ml) to histopathology. As in FIGS. 9a and 9b, the contrast of the tumor in the image is high and the outlined cancerous area, as indicated by arrow 124 in the FPI correlates well with that marked by Mohs surgeon in the frozen section, as indicated by arrow 126. For this specimen the values of fluorescence polarization averaged over the cancerous and normal tissue areas are $(7.1\pm0.3)\times10^{-2}$ and $(2.7\pm0.3)\times10^{-2}$, respectively. For the specimen shown in FIG. 10, the ratio of $S_{fpi}/S_h$=1.06.

Figure 11A:
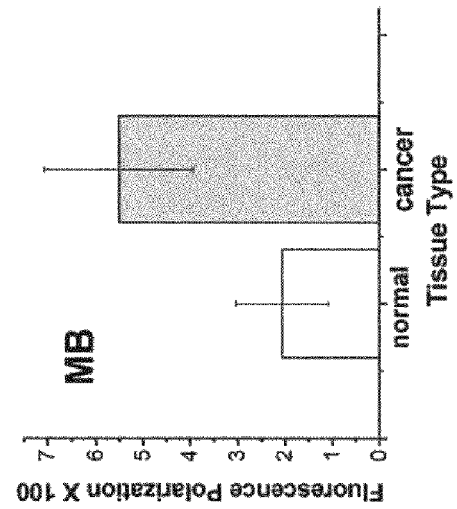
FIG. 11a-11b depict bar graphs illustrating the exogenous fluorescence polarization of cancerous and normal tissue for 15 samples, as discussed herein below, wherein 8 of the samples were stained with TB and 7 of the samples were stained with MB.
Figure 11B:
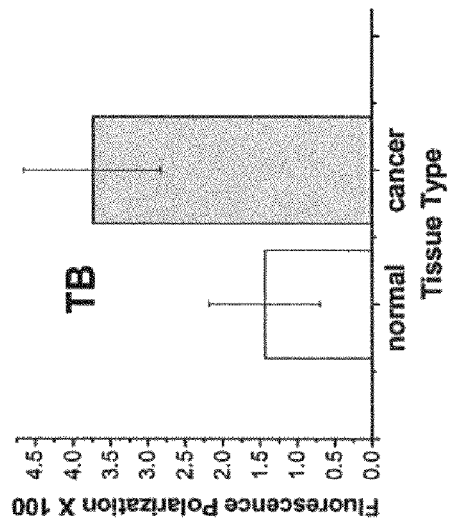

Of the 15 samples, 8 samples were stained in TB and 7 samples were stained in MB. In all cases, the tumors could be easily identified and the FPI correlated well with histopathology. For all the tumors investigated $1.01 \leq S_{fpi}/S_h \leq 1.08$. The average values of fluorescence polarization for cancerous and normal tissue stained with TB and MB are summarized in FIGS. 11a and 11b, respectively. In each sample, the value of fluorescence polarization for diseased and healthy tissue was determined by determining the average over the cancerous and normal areas of the specimen.

Modifications

Although preferred embodiments of the present invention and modifications thereof have been described in detail herein, it is to be understood that this invention is not limited to these embodiments and modifications, and that other modifications and variations may be effected by one skilled in the art without departing from the spirit and scope of the invention as defined by the appended claims.

For instance, the imaging apparatus is not limited to the embodiment shown in FIG. 1. Such apparatus may be included in a single unit or such apparatus may be included in an endoscope.

The difference image $I_\delta=I_\parallel-I_\perp$, can be used as a measure of fluorescence polarization in addition or instead of fluorescence polarization/fluorescence anisotropy image.

Further, although the present invention makes use of TCN and TBO to stain the tissue, many other fluorescent contrast agents can be used to stain the tissue thereby increasing the contrast of the tumor in the images.

For instance, fluorescent chromophores and photosensitizers may be used to enhance imaging contrast. As used herein, a "chromophore" means any light-absorbing chemical compound that is useful for enhancing image contrast by the methods and apparatus described. Chromophores include photosensitizers, drugs, dyes, microparticles, nanoparticles, or stains which absorb light. As used herein, "photosensitizer" means a chemical compound that produces a biological effect upon photoactivation or a biological precursor of a compound that produces a biological effect upon photoactivation. For the purpose of this invention, it is not necessary that a photosensitizer be used. However, many photosensitizers have been developed specifically for their ability to localize within cancerous tumors. Photosensitizers also must absorb light, in order to function as a photosensitizer (i.e. to be activated by light). Therefore, photosensitizers are a useful part of the large number of light-absorbing dyes and drugs, which can be used to enhance image contrast in the present invention.

Porphyrins and synthetic, modified porphyrins have traditionally been used as photosensitizers for photodynamic therapy (PDT). Porphyrins are the backbones of the molecule heme, the chief constituent of hemoglobin, which is the carrier of oxygen in red blood cells. Porphyrins, in an oxygen-rich environment, can absorb energy from photons and transfer this energy to surrounding oxygen molecules. At a specific wavelength corresponding with that of incident light, porphyrin is excited to the singlet excited state ($^1P^*$) This singlet excited porphyrin molecule can decay back to the ground state ($P^0$) with release of energy in the form of fluorescence. If the lifetime of the singlet state is long enough, it is possible for the singlet state to be converted to a triplet excited state ($^3P^*$), which can transfer energy to another triplet state. A molecule that is present in great abundance in cells is oxygen, which naturally occurs in $O_2$ form. This dioxygen molecule has a triplet ground state, and provided that the energy of the $^3P^*$ molecule is higher than that of its product, dioxygen in its triplet state is converted into the highly toxic singlet oxygen.

As stated above, singlet oxygen, as well as free radicals that are also produced during the photoactivation process, is extremely reactive and can damage proteins, lipids, nucleic acids, and other cellular components. Cellular responses to singlet oxygen are complex, but in general, singlet oxygen causes phospholipid peroxidation leading to cell membrane damage and vessel occlusion-mediated ischemia, causing necrosis or apoptosis in the cell of interest. This mechanism of killing differs from cellular damage induced by radiation treatment, where y-radiation is used to generate DNA double strand breaks which if unresolved, will ultimately result in cell death.

Photosensitizers known in the art are selected for therapeutic uses according to: 1) efficacy in delivery, 2) proper localization in target tissues, 3) wavelengths of absorbance, 4) proper excitatory wavelength, and 5) purity, pharmacokinetics, metabolism, and reduced toxicity. Photosensitizers for clinical use are optimally amphiphilic, meaning that it must share the opposing properties of being water-soluble, yet hydrophobic. This is not an absolute requirement for the present invention, but is a preferable characteristic.

When delivered intravenously, a photosensitizer should be water-soluble in order to pass through the bloodstream systemically, however it should also be hydrophobic enough to pass across cell membranes. Modifications, such as attaching polar residues (amino acids, sugars, and nucleosides) to the hydrophobic porphyrin ring, can alter polarity and partition coefficients to desired levels. Similarly, when applied topically (directly) to the tissue prior to imaging in this invention, photosensitizers used as a contrast-enhancing agent may preferentially partition to, adhere to, and/or bind to cancerous tumors or the surrounding normal tissues. In this invention, absorption by the photosensitizer or other light-absorbing dye or drug, is used to enhance image contrast for detection of the tumor.

Photosensitizers of the present invention can bind to lipoproteins that are present in the bloodstream and are transported primarily to cells undergoing rapid division, such as tumors. Rapidly dividing cells require a greater amount of lipoproteins, and as a result, photosensitizers are selectively delivered to these cells at a higher level and with faster kinetics.

Preferably, fluorescent chromophores of the present invention absorb light at one or more wavelength bands in the spectral region between 200 nm and 2000 nm, i.e., the optical part of the electromagnetic spectrum. It is not necessary that the chromophore absorb light at long wavelengths in this spectrum, i.e. at wavelengths, which tend to penetrate deeply into tissue compared with short wavelengths. Chromophores and photosensitizers of the invention can be any known in the art, including, but not limited to, the following:

Tissue Dyes and Stains

A large number of stains and dyes are used in pathology for staining tissue samples prior to imaging with a conventional microscope. Some stains are non-toxic and preferentially bind to cancerous tumors in vivo. These chromophores are called vital stains, and are of particular interest and utility for this invention. In particular, dyes or stains with a delocalized cationic charge are capable of selective binding and retention in tumors. These include rhodamines such as rhodamine 123, phenothiazinium dyes, methylene blue, and toluidine blue. Other vital stains such as rose bengal and eosin, which are red-pink stains binding to collagen in vivo, can be used.

Porphyrins and Hydroporphyrins

Photofrin® (porfimer sodium), hematoporphyrin IX, hematoporphyrin esters, dihematoporphyrin ester, synthetic diporphyrins, O-substituted tetraphenyl porphyrins (picket fence porphyrins), 3,1-meso tetrakis (o-propionamido phenyl) porphyrin, hydroporphyrins, benzoporphyrin derivatives, benzoporphyrin monoacid derivatives (BPD-MA), monoacid ring "a" derivatives, tetracyanoethylene adducts of benzoporphyrin, dimethyl acetylenedicarboxylate adducts of benzoporphyrin, endogenous metabolic precursors, δ-aminolevulinic acid, benzonaphthoporphyrazines, naturally occurring porphyrins, ALA-induced protoporphyrin IX, synthetic dichlorins, bacteriochlorins of the tetra(hydroxyphenyl) porphyrin series, purpurins, tin and zinc derivatives of octaethylpurpurin, etiopurpurin, tin-etio-purpurin, porphycenes, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdins such as, but not limited to zinc methyl pyroverdin (ZNMPV), copro II verdin trimethyl ester (CVTME) and deuteroverdin methyl ester (DVME), pheophorbide derivatives, and pyropheophorbide compounds, texaphyrins with or without substituted lanthanides or metals, lutetium (III) texaphyrin, gadolinium(III) texaphyrin.

Porphyrins, hydroporphyrins, benzoporphyrins, and derivatives are all related in structure to hematoporphyrin, a molecule that is a biosynthetic precursor of heme, which is the primary constituent of hemoglobin, found in erythrocytes. Chlorins and bacteriochlorins are also porphyrin derivatives, however these have the unique property of hydrogenated exo-pyrrole double bonds on the porphyrin ring backbone, allowing for absorption at wavelengths greater than 650 nm. Chlorins are derived from chlorophyll, and modified chlorins such as meta-tetra hydroxyphenylchlorin (mTHPC) have functional groups to increase solubility. Bacteriochlorins are derived from photosynthetic bacteria and are further red-shifted to ~740 nm.

Purpurins, porphycenes, and verdins are also porphyrin derivatives. Purpurins contain the basic porphyrin macrocycle, but are red-shifted to ~715 mm. Porphycenes have similar absorption wavelengths as hematoporphyrin (~635 nm), and are synthetic stable compounds with avidity for cancerous tumors. Verdins contain a cyclohexanone ring fused to one of the pyrroles of the porphyrin ring. Phorbides and pheophorbides are derived from chlorophylls and have been used as PDT drugs; these also can be used as chromophores in this invention. Texaphyrins are new metal-coordinating expanded porphyrins. The unique feature of texaphyrins is the presence of five, instead of four, coordinating nitrogens within the pyrrole rings. This allows for coordination of larger metal cations, such as trivalent lanthanides. Gadolinium and lutetium are used as the coordinating metals.

Cyanine and Other Photoactive Dyes

Merocyanines, phthalocyanines with or without metal substituents, chloroaluminum phthalocyanine with or without varying substituents, sulfonated aluminum PC, ring-substituted cationic PC, sulfonated AlPc, disulfonated and tetrasulfonated derivative, sulfonated aluminum naphthalocyanines, naphthalocyanines with or without metal substituents and with or without varying substituents, tetracyanoethylene adducts, nile blue, crystal violet, azure β chloride, rose bengal, benzophenothiazinium compounds, phenothiazine derivatives including methylene blue.

Cyanines are deep blue or purple compounds that are similar in structure to porphyrins. However, these dyes are much more stable to heat, light, and strong acids and bases than porphyrin molecules. Cyanines, phthalocyanines, and naphthalocyanines are chemically pure compounds that absorb light of longer wavelengths than hematoporphyrin derivatives with absorption maximum at about 680 nm. Phthalocyanines, belonging to a new generation of substances for PDT are chelated with a variety of metals, chiefly aluminum and zinc, while these diamagnetic metals enhance their phototoxicity. A ring substitution of the phthalocyanines with sulfonated groups will increase solubility and affect the cellular uptake. Less sulfonated compounds, which are more lipophilic, show the best membrane-penetrating properties and highest biological activity. The kinetics are much more rapid than those of HPD, with high tumor to tissue ratios (8:1) reached after 1-3 hours. The cyanines are eliminated rapidly and almost no drug remains in the tumor after 24 hours.

Other photoactive dyes such as methylene blue and rose bengal, are also used for PDT. Methylene blue is a phenothiazine cationic dye that is exemplified by its ability to specifically target mitochondrial membrane potential. Specific tumoricidal effects in response to cationic phenothiazine dyes are thought to be due to the electrical potential across mitochondrial membranes in tumor cells. Compared to normal cells, the potential in tumor cells is much steeper, leading to a high accumulation of compounds with delocalized positive charges (i.e. cationic photosensitizers). Rose-bengal and fluorescein are xanthene dyes that can be used in PDT, and as chromophores in this invention. Rose bengal diacetate is an efficient, cell-permeant generator of singlet oxygen. It is an iodinated xanthene derivative that has been chemically modified by the introduction of acetate groups. These modifications inactivate both its fluorescence and photosensitization properties, while increasing its ability to cross cell membranes. Once inside the cell, esterases remove the acetate groups and restore rose bengal to its native structure. This intracellular localization allows rose bengal diacetate to be a very effective photosensitizer.

Other Chromophores

Diels-Alder adducts, dimethyl acetylene dicarboxylate adducts, anthracenediones, anthrapyrazoles, aminoanthraquinone, phenoxazine dyes, chalcogenapyrylium dyes such as cationic selena and tellurapyrylium derivatives, cationic imminium salts, tetracyclines, and anioinic dyes such as Evan's Blue, congo red, and trypan blue.

Immunoconjugates

The chromophore or photosensitizer can optionally be linked to a targeting moiety. In a preferred embodiment, the targeting moiety is an antibody. The antibody component can bind with specificity to an epitope present on the surface of a tumor cell. "Binding with specificity" means that non-cancer cells are either not specifically bound by the antibody or are only poorly recognized by the antibody. The antibodies can comprise whole native antibodies, bispecific antibodies; chimeric antibodies; Fab, Fab', single chain V region fragments (scFv) and fusion polypeptides. Preferably, the antibodies are monoclonal. In this embodiment, the carrier molecule, e.g. antibody, provided additional specificity for binding of the chromophore to tumor cells or other components of cancerous tumors.

Further, the contrast agent used to stain the tissue may, in addition to being applied topically, be given intravenously, subcutaneously or as a pill.

Further, although the above description is directed to the demarcation of nonmelanoma skin cancer, the present invention may be used for imaging any tissue. For instance, it may be used for detection and demarcation of the cancers of other organs or acquire images of the gastrointestinal tract or connective tissue. It may also be used for the demarcation of other skin conditions as well as imaging the mouth, pharynx, and larynx, tracheo-bronchial tree, esophagus, bladder, colon, vagina, cervix, etc.

Although exemplary and preferred aspects and embodiments of the present invention have been described with a full set of features, it is to be understood that the disclosed system, apparatus and method may be practiced successfully without the incorporation of each of those features. It is to be further understood that modifications and variations may be utilized without departure from the spirit and scope of this inventive system, apparatus and method, as those skilled in the art will readily understand. Such modifications and variations are considered to be within the purview and scope of the appended claims and their equivalents. It should also be understood that documents or references cited in this text are expressly incorporated herein by reference.

What is claimed is:

1. A method for imaging a tissue region comprising the steps of:
    applying a fluorescent contrast agent to said tissue region;
    emitting light having a first polarization directly onto the tissue region;
    detecting exogenous fluorescence light remitted from the tissue region having said first polarization direction and exogenous fluorescence light remitted from the tissue region having a second polarization direction perpendicular to said first polarization direction, wherein said remitted exogenous fluorescence light is detected from both normal and diseased tissue in the tissue region;
    forming a total exogenous fluorescence polarization image equal to said detected exogenous fluorescence light having said first polarization direction plus said detected light having said second polarization direction; and
    delineating margins of a lesion from superficial normal tissue in said tissue region by using a difference between the total exogenous fluorescence polarization image of the superficial normal tissue and the lesion.

2. The method of claim 1, wherein a wavelength of the light is 200 nm or 2000 nm, or is in a range between 200 nm and 2000 nm.

3. The method of claim 1, wherein a wavelength of the light is 390 nm or 750 nm or, is in a range between 390 nm and 750 nm.

4. The method of claim 1, further comprising the step of varying a wavelength of the light to form a plurality of images at different depths.

5. The method of claim 1, wherein said total fluorescence image is a total fluorescence anisotropy image.

6. The method of claim 1, wherein said tissue region comprises skin tissue.

7. The method of claim 1, further comprising the steps of acquiring a total endogenous fluorescence polarization image of said tissue region before applying the fluorescent contrast agent, subtracting the total endogenous fluorescence polarization image from the total exogenous fluorescence polarization image to form a total net fluorescence polarization image, and delineating margins of the lesion from the superficial normal tissue in said tissue region by using a difference between the total net fluorescence polarization image of the superficial normal tissue and the lesion.

8. A method for imaging a tissue region comprising the steps of:

emitting light having a first polarization directly onto the tissue region;

detecting endogenous fluorescence light remitted from the tissue region having said first polarization direction and endogenous fluorescence light remitted from the tissue region having a second polarization direction perpendicular to said first polarization direction, wherein said remitted endogenous fluorescence light is detected from both normal and diseased tissue in the tissue region;

forming a total endogenous fluorescence polarization image based on said detected endogenous fluorescence light having said first polarization direction and said detected light having said second polarization direction applying a fluorescent contrast agent to said tissue region;

emitting light having a first polarization directly onto the tissue region;

detecting exogenous and endogenous fluorescence light remitted from the tissue region having said first polarization direction and exogenous and endogenous fluorescence light remitted from the tissue region having a second polarization direction perpendicular to said first polarization direction, wherein said remitted exogenous and endogenous fluorescence light is detected from both normal and diseased tissue in the tissue region;

forming a total exogenous and endogenous fluorescence polarization image equal to said detected exogenous and endogenous fluorescence light having said first polarization direction plus said detected light having said second polarization direction; and subtracting the total endogenous fluorescence polarization image from the total exogenous and endogenous fluorescence polarization image to form a net exogenous fluorescence polarization image; and delineating margins of a lesion from superficial normal tissue in said tissue region by using a difference between the superficial normal tissue and the lesion in the net exogenous fluorescence polarization image.

9. The method of claim 8, wherein a wavelength of the light is 200 nm or 2000 nm, or is in a range between 200 nm and 2000 nm.

10. The method of claim 8, wherein a wavelength of light is 390 nm or 750 nm or, is in a range between 390 nm and 750 nm.

11. The method of claim 8, further comprising the step of varying a wavelength of the light to form a plurality of images at different depths.

12. The method of claim 8, wherein the net exogenous fluorescence polarization image is a total exogenous fluorescence anisotropy image.

13. The method of claim 8, wherein said tissue region comprises skin tissue.

* * * * *